(12) United States Patent
Müller et al.

(10) Patent No.: US 8,322,194 B2
(45) Date of Patent: Dec. 4, 2012

(54) APPARATUS FOR ASCERTAINING AND/OR MONITORING A PROCESS VARIABLE OF A MEDIUM

(75) Inventors: Alexander Müller, Sasbach-Jechtingen (DE); Sascha D'Angelico, Rümmingen (DE); Franco Ferraro, Schwörstadt (DE)

(73) Assignee: Endress + Hauser GmbH + Co. KG, Maulburg (DE)

( * ) Notice: Subject to any disclaimer, the term of this patent is extended or adjusted under 35 U.S.C. 154(b) by 733 days.

(21) Appl. No.: 12/309,471

(22) PCT Filed: Jun. 14, 2007

(86) PCT No.: PCT/EP2007/055908
§ 371 (c)(1),
(2), (4) Date: Oct. 2, 2009

(87) PCT Pub. No.: WO2008/009523
PCT Pub. Date: Jan. 24, 2008

(65) Prior Publication Data
US 2010/0083750 A1   Apr. 8, 2010

(30) Foreign Application Priority Data
Jul. 20, 2006   (DE) .......................... 10 2006 034 105

(51) Int. Cl.
*G01N 11/10*   (2006.01)
*G01N 9/00*   (2006.01)
*G01F 23/00*   (2006.01)

(52) U.S. Cl. ........................ 73/54.27; 73/290 V; 73/32 A

(58) Field of Classification Search ....... 73/54.24–54.27
See application file for complete search history.

(56) References Cited

U.S. PATENT DOCUMENTS

| | | | | |
|---|---|---|---|---|
| 1,458,920 | A | * | 6/1923 | Troll ................................. 177/1 |
| 3,379,644 | A | * | 4/1968 | Katzenstein .................... 252/73 |
| 4,177,669 | A | * | 12/1979 | Wenger ......................... 73/32 A |
| 4,783,987 | A | | 11/1988 | Hager |
| 5,170,856 | A | * | 12/1992 | Yang ............................. 177/209 |
| 5,237,288 | A | * | 8/1993 | Cleveland ..................... 330/107 |
| 5,533,402 | A | * | 7/1996 | Sarvazyan et al. .............. 73/645 |

(Continued)

FOREIGN PATENT DOCUMENTS

DE   101 61 071   6/2003
(Continued)

OTHER PUBLICATIONS

U. Tietze, Halbleiter-Schaltungstechnik, Verlag, 2002.

*Primary Examiner* — Hezron E Williams
*Assistant Examiner* — Nathaniel Kolb
(74) *Attorney, Agent, or Firm* — Bacon & Thomas, PLLC

(57) ABSTRACT

An apparatus for ascertaining and/or monitoring of a process variable of a medium. The apparatus includes: A mechanically oscillatable unit; an exciting/receiving unit, which excites the mechanically oscillatable unit to execute mechanical oscillations and which receives the mechanical oscillations; and an electronics unit, which supplies the exciting/receiving unit with an electrical, output signal, and which receives from the exciting/receiving unit an electrical, input signal. In the electronics unit there is provided an amplifier unit, which amplifies the electrical, input signal to an amplified signal ($S_A$). An adjustable phase shifter is provided, which changes the phase of the amplified signal, and a control unit is also provided, which controls the phase shifter, wherein the control unit measures the frequency of the amplified signal and controls the phase shifter starting from stored data concerning the frequency-phase dependence of the amplifier unit.

8 Claims, 2 Drawing Sheets

U.S. PATENT DOCUMENTS

Figure 1:
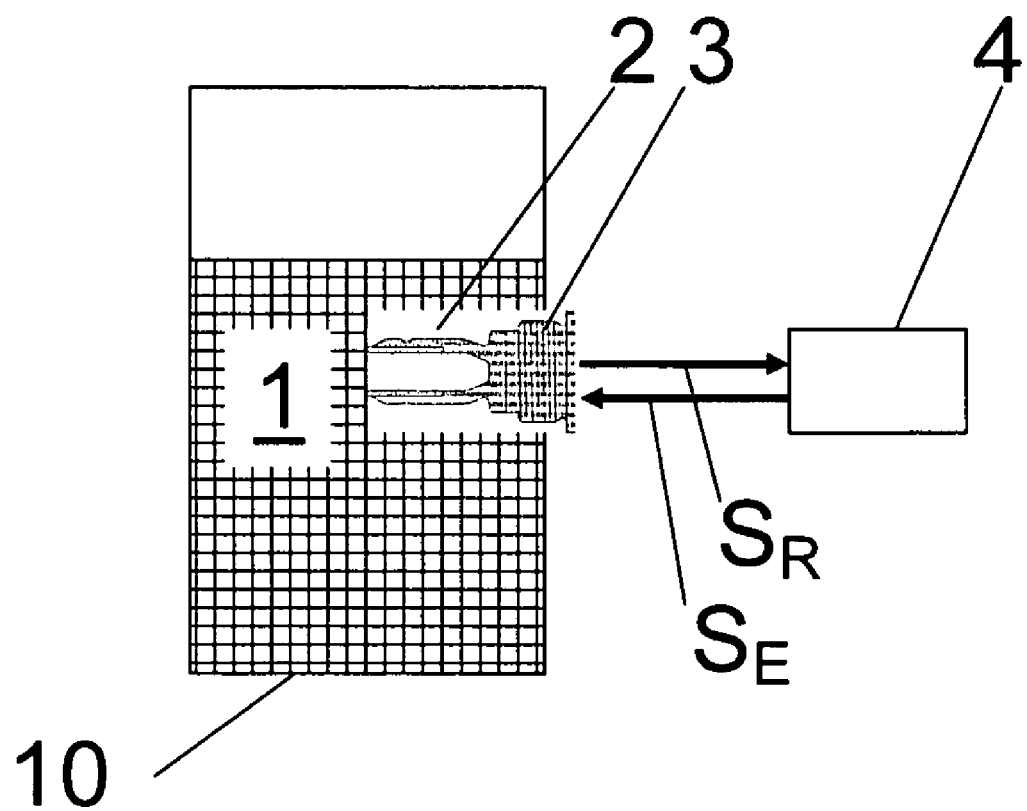

| | | | |
|---|---|---|---|
| 5,837,885 A * | 11/1998 | Goodbread et al. | 73/32 A |
| 5,844,491 A * | 12/1998 | Getman et al. | 340/612 |
| 6,301,973 B1 * | 10/2001 | Smith | 73/861.357 |
| 7,436,100 B2 | 10/2008 | D'Angelico et al. | |
| 2002/0101247 A1 * | 8/2002 | Whynall et al. | 324/460 |
| 2005/0052813 A1 | 3/2005 | Kobayashi | |
| 2005/0140522 A1 * | 6/2005 | Heilig et al. | 340/870.01 |

FOREIGN PATENT DOCUMENTS

| | | |
|---|---|---|
| DE | 10 2005 015 547 | 10/2006 |
| EP | 0 209 872 | 1/1987 |
| EP | 1 580 539 | 9/2005 |
| GB | 2 001 761 | 2/1979 |
| GB | 2 187 286 | 9/1987 |

* cited by examiner

APPARATUS FOR ASCERTAINING AND/OR MONITORING A PROCESS VARIABLE OF A MEDIUM

TECHNICAL FIELD

The invention relates to an apparatus for ascertaining and/or monitoring at least one process variable of a medium in a container. The apparatus includes: At least one mechanically oscillatory unit; at least one exciting/receiving unit, which excites the mechanically oscillatory unit, such that it executes mechanical oscillations, and which receives mechanical oscillations of the mechanically oscillatory unit; and at least one electronics unit, which supplies the exciting/receiving unit with an electrical, exciter signal $S_E$, and which receives from the exciting/receiving unit an electrical, received signal $S_R$. Provided in the electronics unit is at least one amplification unit, which amplifies the electrical input signal $S_R$ to an amplified signal $S_A$. The medium is, for instance, a liquid or a bulk good. The process variable is, for example, fill level, density or viscosity of the medium.

BACKGROUND DISCUSSION

In the state of the art, measuring devices are known, in which a so-called oscillatory fork, as a mechanically oscillatable unit, is excited to execute oscillations. Since the oscillations, i.e. their characterizing variables, such as frequency, amplitude and phase, depend on whether there is contact with a medium, and then on its properties, such as density or viscosity, such variables can be deduced from the characterizing variables of the oscillations. Thus, such a measuring device makes possible, for instance, monitoring fill level or measuring density of the medium.

It has been found that there are ranges of phase differences between the exciting and received signals, in which the behavior of the oscillatory system can be influenced in certain respects. Thus, for instance, detection of foam is enabled or suppressed. Additionally, dependence of the oscillations on changes of viscosity can be eliminated (see DE 100 57 974 A1). In order to achieve these effects, it is, however, necessary, that the desired phase values be achieved as exactly as possible.

SUMMARY OF THE INVENTION

An object of the invention is to provide a measuring apparatus, in which phase between received and exciter signals can be tuned as accurately and reproducibly as possible.

The invention achieves the object in a first variant by features that: at least one tunable phase shifter is provided, which changes the phase of the amplified signal; and at least one control unit is provided, which controls the phase shifter; wherein the control unit is embodied in such a manner, that the control unit measures at least frequency of the amplified signal $S_A$, and that the control unit controls the phase shifter at least starting with stored data concerning frequency-phase dependence of the amplifier unit. The electronics unit includes at least the amplifier unit, the phase shifter and the control unit. Since the input signals $S_R$, before being evaluated, most often first need a conditioning, usually first an amplification and, along with that, most often, a filtering are provided. This so amplified and, in an embodiment, also filtered, signal $S_A$ is, according to the invention, supplied to the control unit. The determining of the phase of this signal, thus, the phase, which results from the amplifier unit, is accomplished via evaluation of the frequency of the signal $S_A$, with the associating of frequency to phase being accomplished via stored data or stored formulas, i.e., on the basis of known behavior of the amplifier unit, frequency of the amplified and/or filtered signal $S_A$ leads to phase, and, therewith, then the phase shifter is suitably controlled. The invention thus enables, that phase no longer exhibits, in each case, a different value, depending on frequency, but, instead, phase has essentially the same value over all frequencies, and such value corresponds to a predeterminable, desired value. I.e., the oscillation excitation is carried out, in each case, with the required, or selectable, phase. This manner of proceeding according to the invention is generically encompassed by the term, "control", in the case of which, starting from the phase shift known from the frequency, the phase is suitably tuned to the desired value.

An embodiment provides, that the control unit evaluates at least the output signal $S_E$, at least with respect to phase, the phase of the output signal $S_E$ is compared with a predetermined phase value, and the control unit controls the phase shifter starting from the comparison. The control thus becomes a quasi closed loop, or feedback, control with respect to phase, wherein the part of the electronics unit between where the signal $S_A$ is tapped and fed to the control unit, and the output signal $S_E$, experiences a closed loop control, while the part between the input signal $S_R$ and the amplified signal $S_A$ is handled by the stored data, or formulas. By this embodiment of the first variant of the invention, there is, thus, a closed loop control over a first section of the electronics unit, in that the result of the phase shifting is compared with the desired value and suitably corrected. Evaluation of the phase of the output signal $S_E$ is accomplished, in such case, for example, by ascertaining the phase difference between the output signal $S_E$ and the amplified signal $S_A$, wherein also the information concerning frequency is required.

The first variant of the invention enables, thus, an open-loop control, or closed loop control, as the case may be, of the phase of a part of the fundamental wave excitation.

In a second variant, the invention achieves the object by the features that: At least one tunable phase shifter is provided, which changes phase of the amplified signal $S_A$; and at least one control unit is provided, which controls the phase shifter; wherein the control unit is embodied in such a manner, that the control unit measures at least the phase difference between the electrical output signal $S_E$ and the electrical input signal $S_R$; and the control unit controls the phase shifter. In this variant, thus, the phase resulting over the entire electronics is measured directly, based on output signal $S_E$ and input signal $S_R$, and the phase shifter is suitable so controlled, that the phase equals the predetermined desired value. A complete closed loop control occurs over the entire electronics, or over the entire oscillatory circuit. For evaluating the input signal $S_R$, such is suitably sampled and digitally filtered, as required, by the control unit, which includes at least one microprocessor. For a monitoring of the phase produced by the electronics unit, for example, in a test phase, the output signal $S_E$ is fed directly to the input of the electronics unit, i.e. without going through the oscillatable unit. By this feedback, thus, directly, the result of the phase tuning can be monitored, or checked. The control unit, which, as in the case of the first variant, is preferably a microcontroller, receives directly the input signal $S_R$ and the output signal $S_E$ and ascertains the phase difference between the two signals. Upon a deviation of this phase difference from a predeterminable desired value, the closed loop control of the phase shifter is activated. This second variant serves, thus, for phase regulation of the complete fundamental wave excitation produced by the electronics unit.

Embodiments applicable to both variants of the invention include that:

The phase shifter is an allpass;

a set of data and/or a formula are/is stored for the frequency-phase dependence of the amplifier unit, with the formula being, for example, a polynomial, or the data being in the form of a stored table of frequency versus phase; and at least one memory unit is provided, in which data concerning the frequency-phase dependence of the amplifier unit are stored, the memory unit being suitably connected with the control unit and being a part thereof.

BRIEF DECSRIPTION OF THE DRAWINGS

Figure 2:
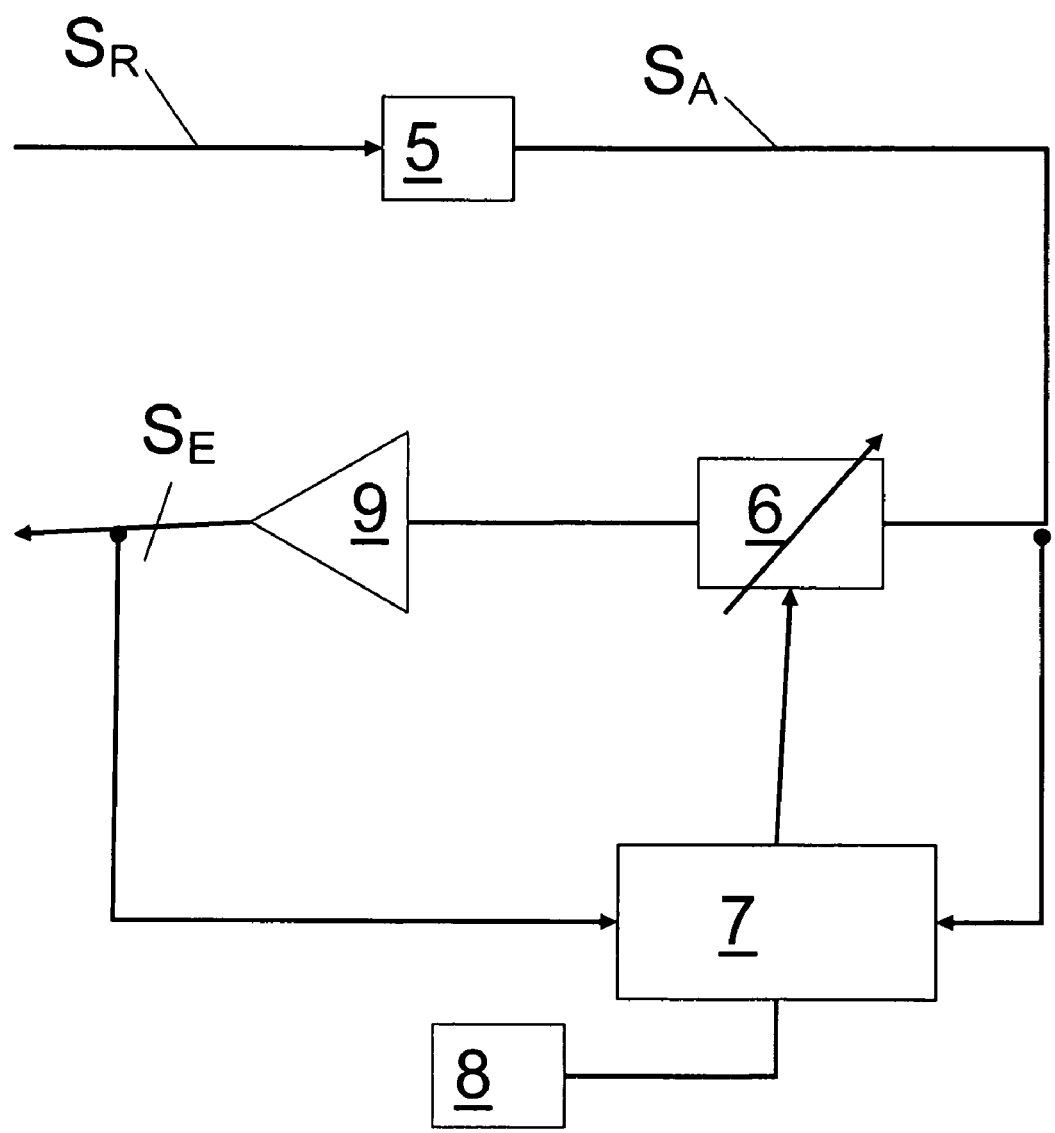

The invention will now be explained in greater detail on the basis of the appended drawing, the figures of which show as follows:

FIG. 1 a schematic representation of the measuring apparatus of the invention in an application; and FIG. 2 a schematic representation of an embodiment of an electronics unit of the measuring apparatus of the invention.

DETAILED DISCUSSION

FIG. 1 shows, schematically, application of a measuring apparatus of the invention. Located in a container 10 is a medium 1, for example, a liquid. In order to monitor the fill level of the medium 1 or to measure, or also monitor, the density of the medium 1, the measuring apparatus with the mechanically oscillatable unit 2 is mounted on the container 10. The mechanically oscillatable unit 2 is, in the illustrated case, an oscillatory fork, i.e. two, so-called fork-tines are mounted on a shared membrane. Behind the membrane is the exciting/receiving unit 3, which functions as a transducer between mechanical oscillations and electrical signals. Here, it is, for example, a piezoelectric element. This exciting/receiving unit 3 is supplied by the electronics unit 4 with an exciter signal $S_E$, an electrical alternating voltage. This signal is converted by the unit 3 into a mechanical oscillation of the mechanically oscillatable unit 2. Conversely, the exciting/receiving unit 3 receives the mechanical oscillations of the oscillatable unit 2 and produces therefrom a received signal $S_R$, which is fed to the electronics unit 4. From the characterizing variables of the received signal $S_R$, in the case of which, likewise, an electrical, alternating voltage is involved, then the process variables of interest are calculated. In order that, for example, viscosity does not affect the oscillations, or in order that, for example, foams are not detected, a special phase value is necessary between the exciter signal $S_E$ and the received signal $S_R$. How this phase is tuned according to the invention is illustrated in FIG. 2.

FIG. 2 shows the components of the invention in the electronics unit 4. The received signal $S_R$ is fed to a first amplifier unit 5, and, as required, also to a filter (not shown). An amplified signal $S_A$, or an amplified and filtered signal $S_A$, as the case may be, is produced. The amplifier unit 5, alone or in combination with a connected filter, exhibits a frequency-phase dependence. This dependence is ascertained in a calibration procedure and suitably stored in a memory unit 8, either as individual pieces of data or by way of a functional relationship. In order that the output signal $S_E$ has the desired phase, a phase shifter 6 is provided, for example, as part of an allpass, which is controlled by the control unit 7. Control is accomplished in such a manner that the amplified signal $S_A$ is fed to the control unit 7, which measures the frequency f of the amplified signal $S_A$. In connection with data stored in the memory unit 8, the control unit 7 controls the phase shifter in such a manner that the desired phase is obtained. For this, it is also necessary, that there be knowledge concerning the further phase behavior of the electronics following from where the signal $S_A$ is tapped, up to the output of the electronics unit 4. For the frequency-phase dependence, for example, a polynomial of second degree is stored. I.e., the phase of the amplified signal output by the amplifier unit 5 is given by $\phi_A = af^2 + bf + c$. This function is obtained by recording the frequency-phase curve of the amplifier unit 5 and then ascertaining the coefficients of the polynomial therefrom. If, furthermore, the output signal $S_E$ should have a special phase $\phi_{des}$, then the phase $\phi_{control}$ to be tuned at the phase shifter is determined by the formula $\phi_{control} = \phi_{des} - \phi_A$. This control can be expanded to a feedback control by feeding also the exciter signal $S_E$ to the control unit 7. In this way, the control unit 7 can determine the phase from the two signals, $S_A$ and the output signal $S_E$, and, with this phase, along with the phase calculated for the amplifier unit 5 via the measurement of the frequency, suitably tune the phase shifter 6. I.e., the electronics unit 4 is quasi close-loop controlled, in that one section is closed-loop controlled and the effects of another section are calculated.

If, from the section of the electronics unit 4, which includes the amplifier unit 5 and, for example, possibly also a filter, a phase $\phi_1$ results, and, from the section following thereon, including at least the phase shifter 6 and the output amplifier 9, a phase $\phi_2$ results, then, over the electronics unit 4, a phase $\phi_{tot} = \phi_1 + \phi_2$ results, which should equal a predetermined, desired value $\phi_{des}$, i.e. $\phi_{tot} = \phi_{des}$.

Phase $\phi_1$ is ascertained from the measured frequency $\nu$ via a known, and earlier measured, functional relationship: $\phi_1 = f(\nu)$. The phase $\phi_2$ results from the comparison of the amplified signal $S_A$ and the output signal $S_E$, i.e. it is measured directly by the control unit 7. In this way, the setpoint for the control of the phase shifter 6 results as follows: $(\phi_2 = \phi_{tot} - \phi_1 = \phi_{des} - f(\nu)$. And, via this closed-loop control, it is possible to have the phase difference between the input signal $S_R$ and the output signal $S_E$ always equal the required desired value, in order to influence the behavior of the oscillatory system in certain ranges, i.e. that there be no effects of changes of viscosity on the frequency of the oscillations or that there be an insensitivity to foam.

The two variants of the invention can be summarized as follows:

In the first variant of the invention, in one embodiment, the frequency of the amplified signal is measured and, on the basis of stored data, phase is tuned via the phase shifter 6. This is thus an open-loop control.

In a second embodiment, the phase difference between the amplified signal $S_A$ and the output signal $S_E$ is measured and phase is adjusted, if required, via the phase shifter. This thus represents a closed-loop, or feedback, control for a section of the electronics unit.

In the second variant, the phase between the output signal $S_E$ and the input signal $S_R$ is measured, and, via the phase shifter, tuned to the required value. This is thus a closed-loop, or feedback, control over the total electronics unit.

The invention claimed is:

1. An apparatus for ascertaining and/or monitoring at least one process variable of a medium in a container, comprising:
   at least one mechanically oscillatable unit;
   at least one exciting/receiving unit, which excites said mechanically oscillatable unit to execute mechanical oscillations and which receives the mechanical oscillations of said mechanically oscillatable unit;
   at least one electronics unit, which supplies said exciting/receiving unit with an electrical, output signal, and which receives from said exciting/receiving unit an electrical, input signal, said electronics unit includes at least one amplifier unit, which amplifies the electrical, input signal to an amplified signal;

at least one tunable phase shifter, which changes the phase of the amplified signal; and at least one control unit, which controls said phase shifter, wherein:

said control unit is embodied in such a manner that it measures at least the frequency of the amplified signal;

said control unit controls said phase shifter at least starting from stored data concerning frequency-phase dependence of said at least one amplifier unit, said control unit evaluates the output signal at least with regard to phase and compares the phase of the output signal with a predetermined value; and said control unit controls the phase shifter starting from the comparison.

2. The apparatus as claimed in claim 1, wherein:
said phase shifter involves an allpass.

3. The apparatus as claimed in claim 1, wherein:
for frequency-phase dependence of said at least one amplifier unit, a set of data and/or a formula is stored.

4. The apparatus as claimed in claim 3, wherein:
at least one memory unit is provided, in which data concerning the frequency-phase dependence of said at least one amplifier unit are stored.

5. An apparatus for ascertaining or monitoring at least one process variable of a medium in a container, comprising:

at least one mechanically oscillatable unit;

at least one exciting/receiving unit, which excites said mechanically oscillatable unit to execute mechanical oscillations and which receives the mechanical oscillations of said mechanically oscillatable unit;

at least one electronics unit, which supplies said exciting/receiving unit with an electrical, output signal, and which receives from said exciting/receiving unit an electrical, input signal, said electronics unit includes at least one amplifier unit, which amplifies the electrical, input signal to an amplified signal;

at least one tunable phase shifter, which changes the phase of the amplified signal; and at least one control unit, which controls said phase shifter, wherein:

said control unit is embodied in such a manner that it measures at least the phase difference between the electrical output signal and the electrical input signal; and said control unit, starting from said measured phase shift, adjusts said phase shift by controlling said phase shifter such that the phrase shift corresponds to a predetermined value.

6. The apparatus as claimed in claim 5, wherein:
said phase shifter involves an allpass.

7. The apparatus as claimed in claim 5, wherein:
for frequency-phase dependence of said at least one amplifier unit, a set of data or a formula is stored.

8. The apparatus as claimed in claim 7, wherein:
at least one memory unit is provided, in which data concerning the frequency-phase dependence of said at least one amplifier unit are stored.

* * * * *